US007706862B2

(12) United States Patent
Alfano et al.

(10) Patent No.: US 7,706,862 B2
(45) Date of Patent: *Apr. 27, 2010

(54) DETECTING HUMAN CANCER THROUGH SPECTRAL OPTICAL IMAGING USING KEY WATER ABSORPTION WAVELENGTHS

(75) Inventors: Robert R. Alfano, Bronx, NY (US); Jamal H. Ali, Brooklyn, NY (US); Wubao Wang, Flushing, NY (US); Manuel Zevallos, Woodhaven, NY (US)

(73) Assignee: Research Foundation of the City University of New York, New York, NY (US)

( * ) Notice: Subject to any disclaimer, the term of this patent is extended or adjusted under 35 U.S.C. 154(b) by 922 days.

This patent is subject to a terminal disclaimer.

(21) Appl. No.: 10/926,556

(22) Filed: Aug. 26, 2004

(65) Prior Publication Data

US 2005/0240107 A1 Oct. 27, 2005

Related U.S. Application Data

(63) Continuation-in-part of application No. 10/825,742, filed on Apr. 16, 2004, now abandoned.

(60) Provisional application No. 60/463,352, filed on Apr. 17, 2003.

(51) Int. Cl.
*A61B 6/00* (2006.01)
*A61B 5/00* (2006.01)
(52) U.S. Cl. .................. 600/473; 600/475; 600/477; 600/310
(58) Field of Classification Search .................. 600/477, 600/473, 475, 476, 310
See application file for complete search history.

(56) References Cited

U.S. PATENT DOCUMENTS 5,131,398 A * 7/1992 Alfano et al. .............. 600/476
5,799,656 A * 9/1998 Alfano et al. .............. 600/473

(Continued)

OTHER PUBLICATIONS

Ion-Christian Kiricuta Jr. et al., "Tissue Water Content and Nuclear Magnetic Resonance in Normal and Tumor Tissues", May 1975, Cancer Research, vol. 35, pp. 1164-1167.*

(Continued)

*Primary Examiner*—Eric F Winakur
*Assistant Examiner*—Katherine L Fernandez
(74) *Attorney, Agent, or Firm*—Cohen Pontani Lieberman & Pavane LLP

(57) ABSTRACT

Spectral optical imaging at one or more key water absorption fingerprint wavelengths measures the difference in water content between a region of cancerous or precancerous tissue and a region of normal tissue. Water content is an important diagnostic parameter because cancerous and precancerous tissues have different water content than normal tissues. Key water absorption wavelengths include at least one of 980 nanometers (nm), 1195 nm, 1456 nm, 1944 nm, 2880 nm to 3360 nm, and 4720 nm. In the range of 400 nm to 6000 nm, one or more points of negligible water absorption are used as reference points for a comparison with one or more key neighboring water absorption wavelengths. Different images are generated using at least two wavelengths, including a water absorption wavelength and a negligible water absorption wavelength, to yield diagnostic information relevant for classifying a tissue region as cancerous, precancerous, or normal. The results of this comparison can be used to identify regions of cancerous tissue in organs such as the breast, cervix and prostate.

26 Claims, 17 Drawing Sheets

U.S. PATENT DOCUMENTS

| | | | | |
|---|---|---|---|---|
| 5,847,394 | A * | 12/1998 | Alfano et al. | 250/341.8 |
| 6,205,353 | B1 * | 3/2001 | Alfano et al. | 600/476 |
| 6,240,312 | B1 * | 5/2001 | Alfano et al. | 600/476 |
| 6,665,557 | B1 * | 12/2003 | Alfano et al. | 600/473 |
| 2004/0116814 | A1 * | 6/2004 | Stranc et al. | 600/473 |

OTHER PUBLICATIONS

J. Rosai, Ackerman's surgical pathology, vol. 2, Mosby Incorporated, CA (1998). The Section of "Carcinoma" in Chapter 18, "Male reproductive system and prostate and seminal vesicles", pp. 931-939.

Dudley Williams, "Frequency assignments in infra-red spectrum of water, "Nature" vol. 210, 194-195 (1966).

C.H. Liu et al., "Raman, fluorescence and time-resolved light scatterings as optical diagnostic techniques to separate diseased and normal biomedical media", J. Photochem. Photobiol. B: Biol., vol. 16, 187-209 (1992).

W. B. Wang et al., "Spectral polarization imaging of human prostate tissues", Proceedings of SPIE, vol. 3917, 75-78 (2000).

* cited by examiner (a) P=600 nm
D=600 nm (b) P=700 nm
D=700 nm (c) P=800 nm
D=800 nm Table 1

| λ(nm) | O.D. | | | T | | | $\mu_t$ cm$^{-1}$ | | |
|---|---|---|---|---|---|---|---|---|---|
| | C | N | W | C | N | W | C | N | W |
| 700 | 1.50 | 2.14 | 0.0062 | 0.0326 | 0.0074 | 0.9858 | 104 | 149 | 0.433 |
| 800 | 1.37 | 1.89 | 0.0077 | 0.0440 | 0.0132 | 0.9824 | 95 | 131 | 0.5380 |
| 1200 | 1.10 | 1.25 | 0.0185 | 0.0818 | 0.0577 | 0.9583 | 76 | 86 | 1.29 |
| 1450 | 1.36 | 1.61 | 0.1394 | 0.0451 | 0.0252 | 0.7254 | 94 | 112 | 9.70 |

Table 2

| Wavelength (nm) | $D_{Normal}$ | $D_{Cancer}$ |
|---|---|---|
| 700 | 0.079 | 0.059 |
| 800 | 0.100 | 0.088 |
| 1200 | 0.761 | 0.435 |
| 1450 | 0.849 | 0.749 |

DETECTING HUMAN CANCER THROUGH SPECTRAL OPTICAL IMAGING USING KEY WATER ABSORPTION WAVELENGTHS

CROSS REFERENCE TO RELATED APPLICATION

This application is a continuation-in-part of U.S. patent application Ser. No. 10/825,742 which was filed with the U.S. Patent and Trademark Office on Apr. 16, 2004 now abandoned. This application claims priority from U.S. Provisional Patent Application Ser. No. 60/463,352 which was filed on Apr. 17, 2003. The contents of the patent application and provisional patent application are incorporated herein in their entirety by reference.

BACKGROUND OF THE INVENTION

1. Field of the Invention

The invention is directed to spectral optical imaging methods and, more specifically, to optical imaging techniques for detecting human cancer in prostate and other tissues.

2. Description of the Related Art

Cancer is a disease that is characterized by uncontrolled cellular growth, whereby cancer cells continue to grow and divide in an abnormal manner. A tumor, defined as any abnormal growth of cells, may be classified as benign or malignant. A benign tumor remains confined or localized to a given site, whereas a malignant tumor is capable of invading other tissues or organs. Most cancers fall into one of three main groups: carcinomas, sarcomas, and leukemias/lymphomas. Of these groups, the most frequently-occurring cancers are carcinomas. Carcinomas may develop from cells that cover the surface of the body, cells of the internal organs, and glandular cells. Glandular cells are found, for example, in the breast and the prostate. Sarcomas are cancers of connective tissue, such as muscle and bone. Leukemias are cancers of the blood forming cells and cells of the immune system.

All cells consist of two major parts: a nucleus and a cytoplasm. The nucleus is the cell's manager. It contains the cell's genetic material in the form of strands of deoxyribonucleic acid (DNA). The cytoplasm, a fluid within the cell, contains proteins, carbohydrates, lipids, and nucleic acids in a water-based solution. A change or mutation in the expression of genes causes cancer to occur. In molecular terms, cancer is a genetic change that occurs within the cell. Two distinct classes of cancer-related genes have been identified: oncogenes and tumor suppressor genes.

Lung cancer, rectum cancer, breast cancer, prostate cancer, urinary cancer, oral cancer, brain cancer and skin cancer represent some of the most frequently occurring cancers. For men, the most common type of cancer is cancer of the prostate. The risk of prostate cancer increases with age. Accordingly, early detection of cancer plays a vital role in reducing mortality from prostate cancer. Present-day screening methods for prostate cancer include digital rectal examinations and prostate specific antigen (PSA) blood tests. There are several different grades or stages of cancer, and these may be ranked using a well-known scale that classifies cancerous and precancerous regions into any of five Gleason Grades, denoted as Stages 1, 2, 3, 4 and 5. Precancerous stages (denoted as stages 1 and 2) correspond to the early stages of cancer.

In an attempt to develop less invasive diagnostic procedures, recent efforts have been directed towards utilization of near-infrared (NIR) optical spectroscopy for cancer and pre cancer detection. NIR techniques, based upon an understanding of cancer at the molecular level, represent an important step toward early detection of cancer. The optical spectrum of a tissue sample contains information about the biochemical composition of that tissue. A primary objective of NIR is to distinguish molecular bonding within cancerous tissue from molecular bonding within normal tissue by detecting fluorescence and Raman spectra from native molecular markers. A gene that is responsible for prostate cancer is attached or tagged with a certain chromophore (molecular marker), such as dye or semiconductor quantum dots, to enhance contrast and resolution in the NIR optical spectroscopy imaging process. The use of molecular markers could enable the imaging process to penetrate more deeply into tissue under examination, thereby enabling doctors and other diagnostic personnel to obtain more information.

State-of-the-art of present techniques for detection of prostate cancer provide limited contrast, low resolution images that do not enable an accurate identification of cancerous tissue. For this reason, the digital rectal examination (DRE), ultrasound imaging, and prostate specific antigen (PSA) blood test are currently the most commonly utilized methods for early detection of prostate cancer. Although X-rays, ultrasound, and magnetic resonance have also been used to detect tumors, these techniques have limited detection capabilities and/or create safety concerns. For example, X-rays are not well-suited for the detection of tumors less than 1 mm in size and, moreover, represent a safety hazard to the patient.

Optical spectroscopy techniques including fluorescence, Raman scattering and light scattering have been used to investigate normal, benign, precancerous and malignant tissues. For example, NIR spectral polarization imaging has been used to image foreign objects dyed with Indocyanine Green at different depths inside prostate tissues. Some disadvantages of fluorescence and Raman scattering methods are a) a point-by-point evaluation cannot be performed; b) a weak diagnostic signal is provided, relative to the amount of elastic scattering that occurs; and (c) direct contact with cancerous tissue must occur in order to make a diagnosis. Elastic scattering detection examines melanin and hemoglobin absorption by focusing on the ultraviolet (UV) and visible regions of light. In these spectral regions, light is highly scattered, making it difficult to detect any microstructure changes that may occur in a tissue sample.

For the sake of computational expediency, a simplification known as the "diffusion approximation" has been widely utilized for describing light propagation in biological media, especially when scattering dominates absorption and the radiant energy fluence rate close to the source is not known. Transport theory is based upon a radiative transfer equation. The solution of this transfer equation in a highly absorbing medium, such as water, surrounded by the non-absorbing tissue, can be simplified and described by the Beer-Lambert law. Note that water absorption is stronger than scattering at specific wavelengths. The attenuation due to absorption is proportional to the concentration (C) of chromophores in tissues, such as water molecules or a specific dye. The optical path length (d) is described by:

$$I = I_0(1-R) e^{-acd} \quad \text{or} \quad A = \ln\frac{I_0(1-R)}{I} = acd \qquad (1)$$

where A is the attenuation measured in optical densities, $I_0$ is the light intensity incident on the medium, l is the light intensity transmitted through the medium, a is the specific extinction coefficient of the absorbing compound in micromolars per cm, c is the concentration of the absorbing compound in micromolars, and d is the distance between the points where the light enters and leaves the medium (sample thickness). The product (ac) is known as the absorption coefficient ($\mu_a$) of the medium. R is the specular reflection coefficient (Fresnel reflection) from the surface of the sample. When adding absorbing molecules to a host turbid medium (such as tissue), the backscattered or transmitted signal from the sample (water/chromophore-tissue) will be less, especially when absorption dominates.

To calculate the absorption coefficient of a tissue sample, the transmittance (T) or optical density (O. D., $T=I/I_0(1-R)= 10^{-O.D.}$) of a thin specimen (such as prostate tissue) can be measured in the ballistic region. In a very thin specimen where multiple scattering is negligible, such that $d \leq l_s$ ($l_s$ is the scattering length), or where absorption is much stronger than scattering, the measured absorption coefficient can be obtained from:

$$\mu_a = \frac{1}{d} \ln\left(\frac{1}{T}\right), \text{ where } T = \frac{I}{I_0(1-R)}. \quad (2)$$

In relatively thicker tissues, the total attenuation coefficient of a ballistic layer ($\mu_t = \mu_s + \mu_a$) is measured.

Pursuant to Fresnel's laws of reflection, specular reflection of incident light from a surface is a function of polarization, incident angle, and index of refraction. In the case of unpolarized light, the reflected radiance from a surface is written as $$R(\theta_i) = \frac{1}{2}[R_{II}^2 + R_\perp^2] \quad (3)$$

where $\theta_i$ is the incident angle, $R_{II}$ is the reflected electric field parallel to the plane of incidence, and $R_\perp$ is the reflected electric field perpendicular to the plane of incidence. For normal incidence ($\theta_i=0$), equation (3) becomes $$R(0) = \left(\frac{n_i - n_t}{n_i + n_t}\right)^2 \quad (4)$$

where $n_i$ is the index of the incident medium, and $n_t$ is the index of the transmitted medium.

A linearly polarized light incident on tissue loses its polarization as it traverses the medium for an order of transport length $l_{tr}$, where $$l_{tr} = \frac{l_s}{(1-g)},$$

and g is an anisotropy factor. A small portion of the incident light is backscattered by epithelial cells, such that the backscattered light retains its polarization in this single scattering event. The remaining light diffuses into the underlying tissue and is depolarized by multiple scattering. The degree of polarization is defined as:

$$D=(I_{||}-I_\perp)/(I_{||}+I_\perp) \quad (5)$$

where the $I_{||}$ and $I_\perp$ are the intensities for the parallel and perpendicular components of the reflected or scattered light from the object, respectively.

The contrast is the difference in light intensity in an object or image, and defined as:

$$C=(I_{max}-I_{min})/(I_{max}+I_{min}) \quad (6)$$

where the $I_{max}$ and $I_{min}$ are the maximum and minimum intensities of light recorded from the object, respectively.

Scattering and absorption of tissue is caused by the presence of a cellular nucleus (~10 µm), nuclei (~3 µm), mitochondria (length ~1 µm), blood cells, glogi (complicated shapes), cytoplasm, and other tissue structures. The size of the scatterer and the incident wavelength determine the type of scattering that will occur. Also, the distribution of the scatterer size is an important factor in evaluating scattering intensity versus angle $$\left(\theta \sim \frac{\lambda}{a}\right).$$

The optical parameters of tissues, such as refractive index n, scattering coefficient $\mu_s$, and absorption coefficient $\mu_a$, are responsible for the degree of light scattering in tissue.

SUMMARY OF THE INVENTION

A primary object of the invention is to provide a minimally invasive diagnostic technique for differentiating normal tissue from cancerous and precancerous tissue.

Another object of the present invention is to detect changes in water content in normal and cancer tissues.

Another object of the invention is to utilize spectral optical imaging, elastic scattering, and polarization imaging techniques to provide images of sufficient quality so to aid in diagnosing cancerous tissue.

Still another object of the invention is to utilize spectral optical imaging techniques to provide reliable noninvasive diagnosis of prostate and breast cancer.

These and other objectives of the invention are achieved by using spectral optical imaging in the near infrared (NIR) at one or more key water absorption wavelengths to identify any difference in water content between a region of cancerous or precancerous tissue and a region of normal tissue. Water content is an important diagnostic parameter. Our work using spectral polarization imaging and spectroscopy can measure the difference in water content between normal and cancer tissues. Our measurements show that the tissues in the early stages of prostate cancer have less water content than normal tissues. Tissue regions in the later stages of cancer have more water content than normal tissues. The key water absorption "fingerprint" wavelengths include at least one of 980 nanometers (nm), 1195 nm, 1456 nm, 1944 nm, 2880 nm to 3360 nm, and 4720 nm. In the range of 400 nm to 6000 nm, at least one reference wavelength of low or no water absorption—illustratively, 4500 nm, 2230 nm, 1700 nm, 1300 nm, 1000 nm, and 800 nm—is used to generate at least one reference image for drawing a comparison with at least one image taken at one or more key water absorption wavelengths. The results of this comparison are used to identify regions of cancerous tissue, illustratively in organs such as the breast and the prostate.

Pursuant to a further embodiment of the invention, imaging at key water absorption wavelengths of approximately at least one of 980 nm, 1195 nm, 1944 nm, 2880 nm to 3360 nm, and 4720 nm is performed to diagnose a tissue region for prostate, breast, or other cancer by observing changes in optical density (O.D.) images of the region due to water content. A reference image is generated using at least one non water absorption wavelength, illustratively 800 nm and 1000 nm. The reference image is compared with one or more images generated at the key water absorption wavelengths on a pixel-by-pixel basis to generate a difference image. The difference image (such as between 980 nm and 800 nm) is simplified by: $I_{980}(x,y)-I_{800}(x,y)=\Delta I$, where I represents the intensity of each pixel (x and y) in the image and $\Delta I$ represents the image difference between the two chosen wavelengths (800 nm and 980 nm in this example) at substantially the same pixel location.

TABLE 1 sets forth calculated extinction coefficients ($\mu_t$), optical densities (OD), and transmission (T) for human prostate normal tissue (N), human prostate cancerous tissue (C), and water (W).

Figure 9:
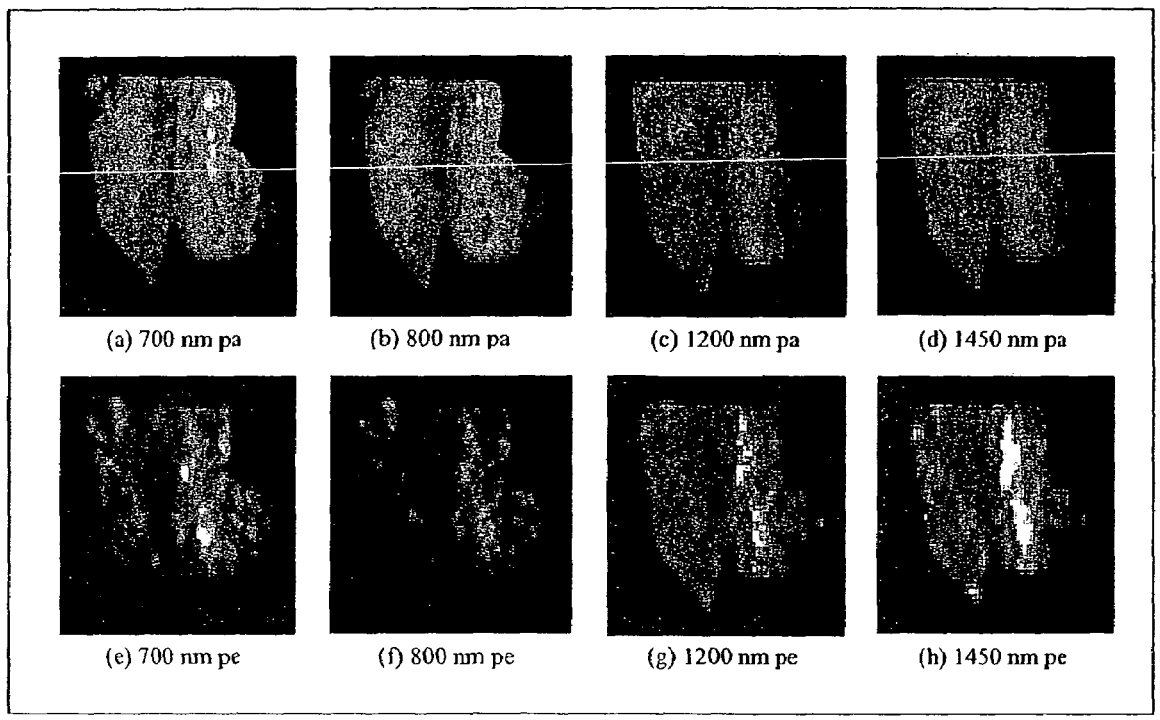
FIG. 9 shows transmission images of the specimen of FIG. 2 at several wavelengths along a parallel plane and a perpendicular plane.

TABLE 2 sets forth the degree of polarization of the normal and cancerous cells shown in FIG. 9 as a function of wavelength.

DETAILED DESCRIPTION OF THE PRESENTLY PREFERRED EMBODIMENTS

The most abundant constituent of tissue is water. Approximately 78% of the human body is water, with the effect that water is a universal solvent for most biological tissues. At the molecular level, one interesting characteristic of water is that it is a polar substance, such that one portion of the molecule carries a negative charge and another portion carries a positive charge. This property is important in the context of cancer diagnosis. Cancerous tissues have a lower degree of organization and different water content relative to normal tissues. In cells, water is essential for converting mechanical energy generated by contractile proteins into chemical energy that is useful for various metabolic processes. Regulating water volume within a living cell, contractile proteins mechanically control ion selectivity, ion accumulation, and electron transport in mitochondria. When the availability of water in the cell is increased, this causes a corresponding increase in the dielectric constant of the medium, signifying that the energy needed in ion exchange is minimized when intracellular water is abundant.

In men, prostate cancer has a high incidence of occurrence as well as a high mortality rate. Every year, nearly 180,000 new prostate cancer cases are diagnosed, and about 37,000 deaths annually are caused by prostate cancers in U.S. Current methods for monitoring the prostate include a prostate specific antigen (PSA) blood test, a digital rectal examination (DRE), and transrectal ultrasound (TRUS). The PSA tests and DRE exams frequently result in false positives. The positive predictive value of TRUS is low, and its spatial resolution is poor. When the PSA level is elevated or the DRE abnormal, there is a one-in-three chance that cancer is present. Cancer can only be confirmed by a needle biopsy of the prostate. In the biopsy, a number of cores of prostate tissue are taken with a thin needle guided into selected regions of the prostate with an ultrasound probe. Since ultrasound imaging has poor spatial resolution and limited accuracy, and needle biopsy is invasive, better approaches are needed to provide high resolution images in a noninvasive way, so as to enable detection of prostate tumors at an early stage. There are five different grades or stages of cancer, oftentimes referred to as stages 1, 2, 3, 4 and 5. Stages 1 and 2 are the early stages of cancer, and are used to denote precancerous tissues.

Extensive research has focused on nuclear magnetic resonance spectroscopy (NMR) techniques. Basically, NMR detects signals generated by the nuclear spins of protons, such as the protons (H+ ions) of water. NMR spectroscopy has been used to study water in muscle tissue. It has been shown that the water spectrum of rat or mouse skeletal muscle is broader than that of pure water, due to the higher order phases of water. This restriction is due to interactions between water molecules and cellular or other macromolecules.

Figure 1:
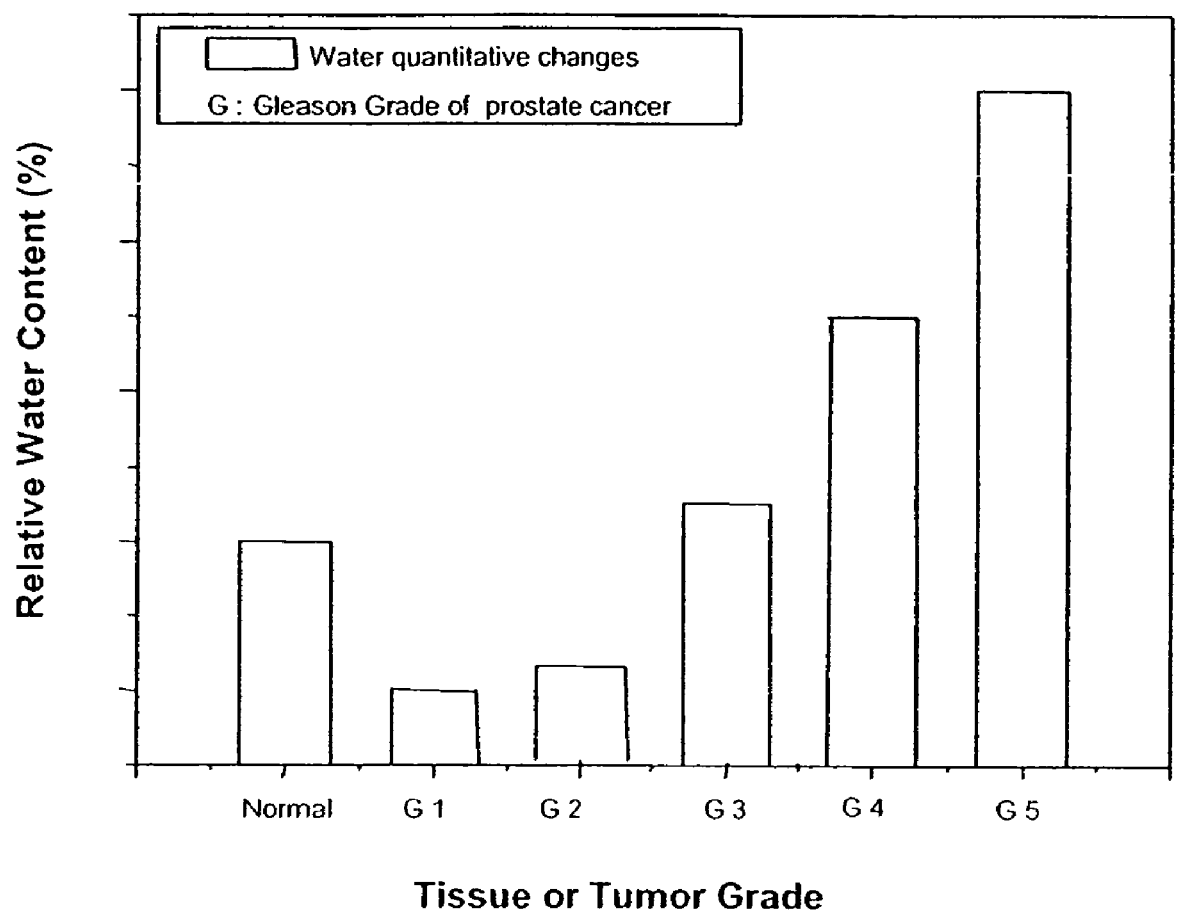
FIG. 1 is a bar graph showing the relative water content of normal, precancerous, and cancerous tissues for each of a plurality of Gleason stages.

The spectral properties of light propagating in tissues can be used to evaluate the cancerous state of tissues. Under light illumination, normal and cancerous prostate tissues absorb and emit different light, each with unique fingerprint spectra. About 95% of prostate cancers are categorized as adenocarcinoma, including large duct cell, endometrial type (endometrioid), mixed edenocarcinoma, mucinous, adenosquamous and adenoid cystic carcinoma. As shown in FIG. 1, these cancers contain less water at the early stages (Gleason stages 1 and 2) and, therefore, feel harder and more condensed than normal tissue.

We have studied differences in absorption, emission and scattering between normal and cancerous tissues, and have developed tissue scattering light imaging, tissue emission light imaging and contrast agent emission light imaging techniques, which significantly enhance the visibility of an object hidden within tissues from several millimeters to a few centimeters using 700 to 1000 nm radiation.

The interaction between light and tissue is wavelength dependent. Well-defined wavelengths are absorbed by chromophores, such as proteins, water, and adipose that are naturally present in tissue. Water is involved in various chemical reactions that are activated by light. Bonding of water molecules to other components in tissues give rise to a 3434 $cm^{-1}$ absorption peak, which is essentially a shift in the —OH absorption peak to 3434 $cm^{-1}$ due to formation of H(hydrogen) bonds between water and tissue. The development of NIR and mid-IR spectroscopy techniques to detect the presence of water in tissues offers a safe, non-invasive monitoring of the state of tissue, representing a landmark achievement in the field of medicine. The magnitude of the aforementioned absorption is directly related to the concentration of water in a biological sample. The monitoring of water concentration may be advantageously exploited to determine the state of tissue, thus aiding in the diagnosis of cancerous, precancerous, and normal tissues.

Scattered intensity is related to R, where R is the specular reflection coefficient for Fresnel reflection from the surface of a tissue sample, as was previously discussed in connection with equation (4). The index of refraction, n, of the tissue is substantially in the range of ($1.33 \leq n \leq 1.5$), where n takes the minimum value in this range when the content of water in tissue is maximum (100% water in tissue), and n takes the maximum value in this range when the content of water is minimum (0% water in tissue). The refractive index of a tissue is proportional to its water content, and is given by:

$$n \approx 1.5 - (1.5 - 1.33)V \qquad (7)$$

where V is the volume fraction of water. The index of refraction of cancerous tissue is higher than that of normal tissue at early stages, since the content of water in the cancerous cells is less than that of the normal cells. Accordingly, the backscattered light from cancerous cells is expected to be larger than that from normal cells. For advanced cancerous stages, the water increases give rise to lower indices of refraction. The backscattered light in such cases will be less.

The nuclei of cancerous cells, as well as those of normal cells, are considered to be much larger than the wavelength of incident light. Therefore, these nuclei obey Mie scattering, resulting in a strong forward scattering of incident light. Since the nuclei of cancer cells are larger than the nuclei of normal cells, the forward scattering intensity of cancerous cells is of greater magnitude than that of normal cells. So, the overall light transmission of cancerous cells is greater than that of normal cells.

The techniques of the present invention are based upon the overall concept that, in order to detect regions of cancerous tissue, one must realize that the amount of water contained within normal tissues differs from the amount of water contained within neoplastic tissues. There is a lack of water in neoplastic tissues relative to the water content of normal tissues during the early stages. Visible to mid-infrared (mid-IR) absorption is directly related to the concentration of water in a biological sample. Monitoring the concentration of water enables a determination of whether or not regions of cancerous tissue are present. Optical images can be performed at pairs of wavelengths: one at an absorption wavelength of $H_2O$ and another at an off-absorption wavelength of $H_2O$. Difference images generated from the absorption wavelength and off-absorption wavelength images can be used to locate tissues in different stages of cancer.

A critical marker for locating cancerous regions in human prostate, breast, and other tissues is the amount of water detected in these tissues by means of transmission and backscattering of specific key wavelengths of visible to mid-infrared (IR) light using polarization imaging techniques. Optical interaction in the tissue due to intermolecular bonding by the —OH portion of water molecules is detected by visible to mid-IR spectroscopy, thus distinguishing localized regions of low water concentration in cancerous and precancerous tissues from other regions of normal water concentration that occur in normal tissues. By using water as a key marker to differentiate normal and cancerous tissue regions, significant progress can be made towards the development of optical non-invasive medical diagnosis in cancer research.

The techniques of the present invention are based upon a realization that differences in light absorption are attributable to —H and —OH bonding in tissue. In turn, the extent of —H and —OH bonding is directly related to the water content of the tissue under test. Typically, there is a reduction of water content in cancerous and precancerous tissue regions relative to that of normal and benign tissues in early stages, while the reverse is true in later cancerous stages. The difference in light absorption, resulting from the differing amounts of water present in normal and cancerous tissues, can be used to diagnose a tissue region as cancerous, precancerous, or normal.

EXPERIMENTAL METHODS

Figure 2:
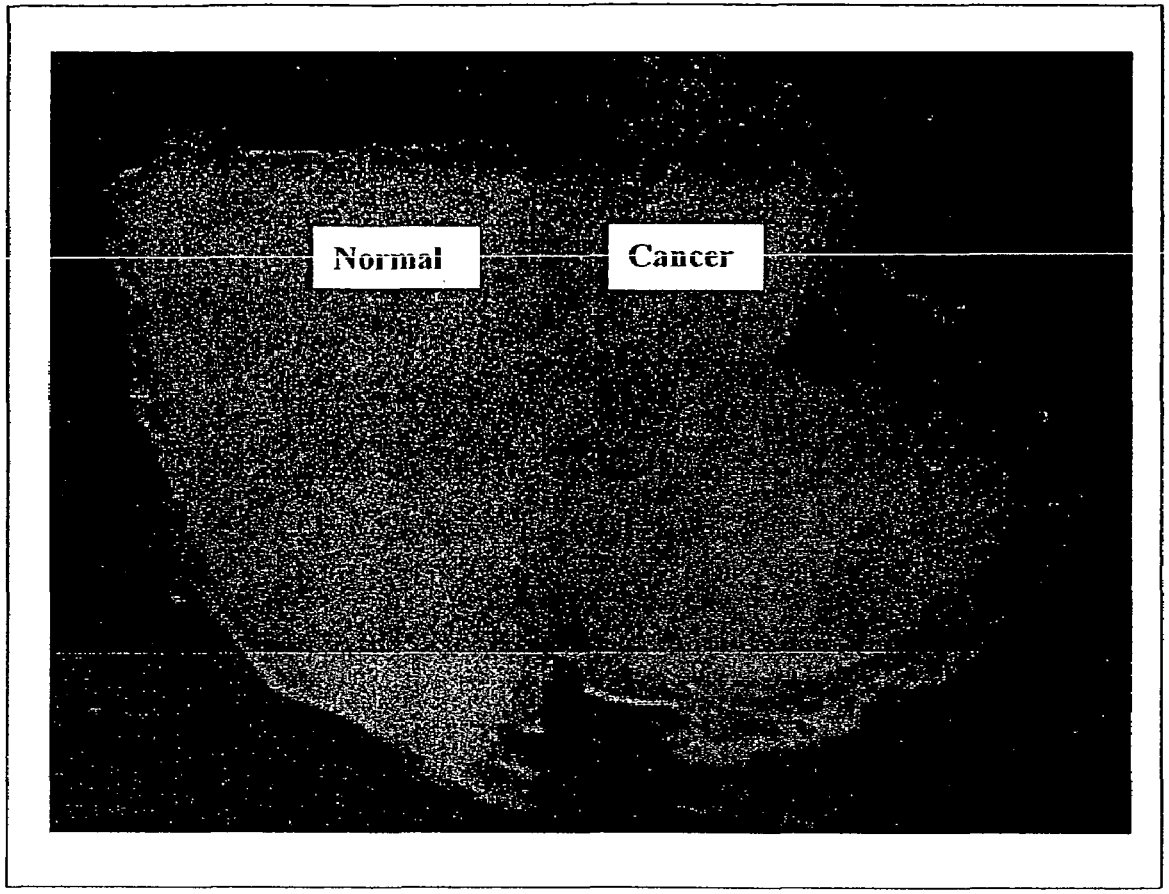
FIG. 2 is a photograph illustrating a typical specimen of human prostate tissue.

Prostate tissue specimens were obtained from the National Disease Research Institute (NDRI) under IRB at the City Colleges of New York (CCNY). A photograph of a typical sample of human prostate tissue is shown in FIG. 2. This photograph was taken using a conventional digital camera. Sample thickness is about 330 µm, and the area of the sample is approximately 2×3 $cm^2$. Throughout the various drawings, samples are arranged, if possible, such that the right hand side of the specimen contains predominately cancerous tissue, while the left hand side contains predominately normal tissue.

The light absorption spectra of the normal prostate tissue, the cancerous prostate tissue, and water were measured using a Perkin-Elmer Lambda 9 UV/VIS/NIR Spectrophotometer with accompanying software. Wavelengths in the approximate range of 400 nm and 25 µm were utilized for this measurement process.

Figure 3:
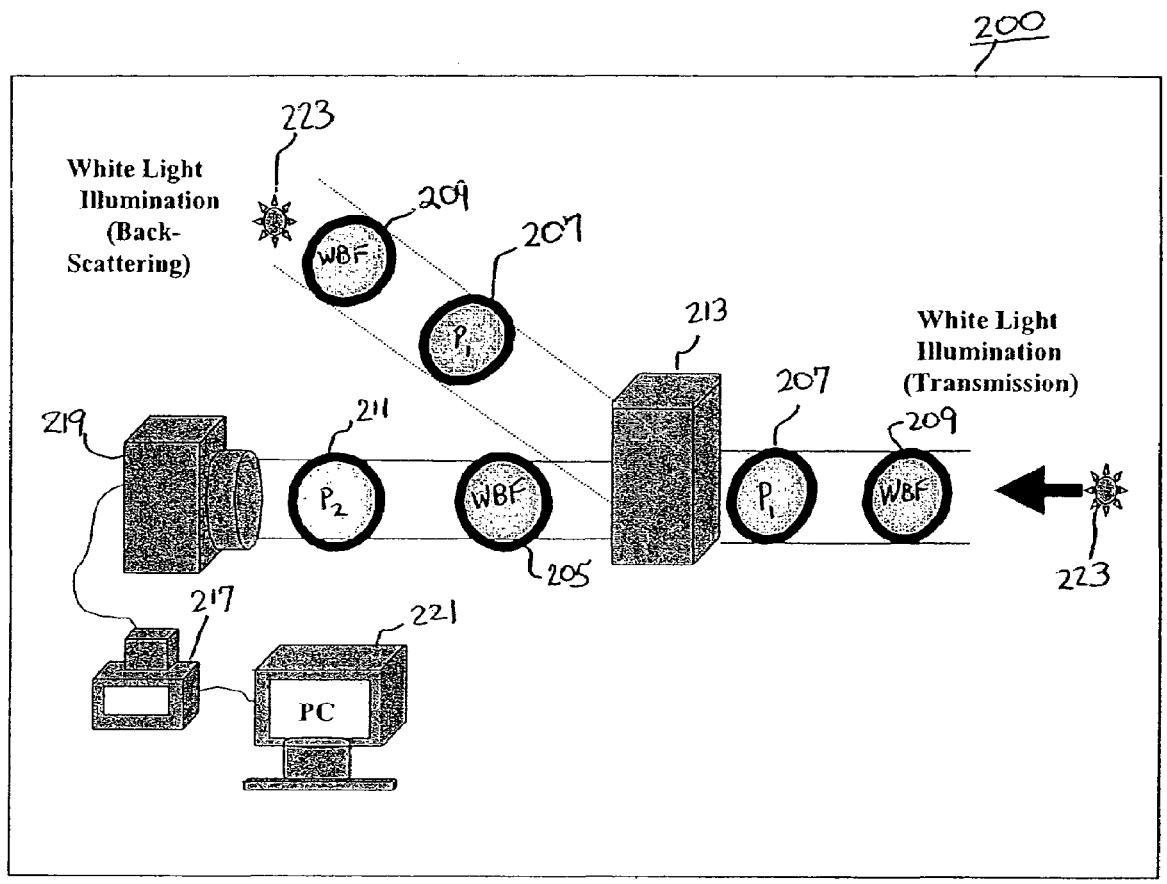
FIG. 3 is a functional hardware block diagram of a spectral polarization imaging system for use with the techniques of the present invention.

Images of scattered light from human prostate samples were measured using a spectral polarization imaging system 200 as shown in FIG. 3. The system is capable of providing images using transmission geometry as well as a back-scattering geometry. When the transmission geometry was employed for imaging measurements, a white light beam 223 having a diameter of approximately 2 cm was used to illuminate a sample 213. Pursuant to transmission geometry, the sample was positioned between the white light beam and a charge-coupled-device (CCD) camera 219. On the other hand, when the back-scattering geometry was used for imaging measurements, white light beam 223 was used to illuminate sample 213 from a direction such that some of the light scattered by sample 213 would reach CCD camera 219.

In both the transmission geometry and the back-scattering geometry, wideband filters (WBF) 205, 209 having a selectable bandpass for admitting any one of several different wavelengths, such as 700 nm, 800 nm, 1200 nm, and 1450 nm, were used to select the desirable spectral range of the illumination and the detected light. A first polarizer ($P_1$) 207 was located in the incident light beam pathway to obtain a linearly polarized illumination light. A second polarizer ($P_2$) 211 was positioned in front of CCD camera 219 for selecting polarization direction to be detected, which may be either parallel or perpendicular relative to the orientation of first polarizer ($P_1$) 207. In the visible and NIR range (600-900 nm), CCD camera 219 was implemented using a cooled CCD Silicon camera (Photomatrix CH250) equipped with a zoom lens of 50-mm focal length to record images in the transmission and backscattering geometries. In the range of 1200 nm to 1450 nm, CCD camera 219 was implemented using an InGaAs NIR CCD camera. The images formed in CCD camera 219 will be recorded by a computer 211 through an electronic control unit 217.

EXPERIMENTAL RESULTS

Figure 4:
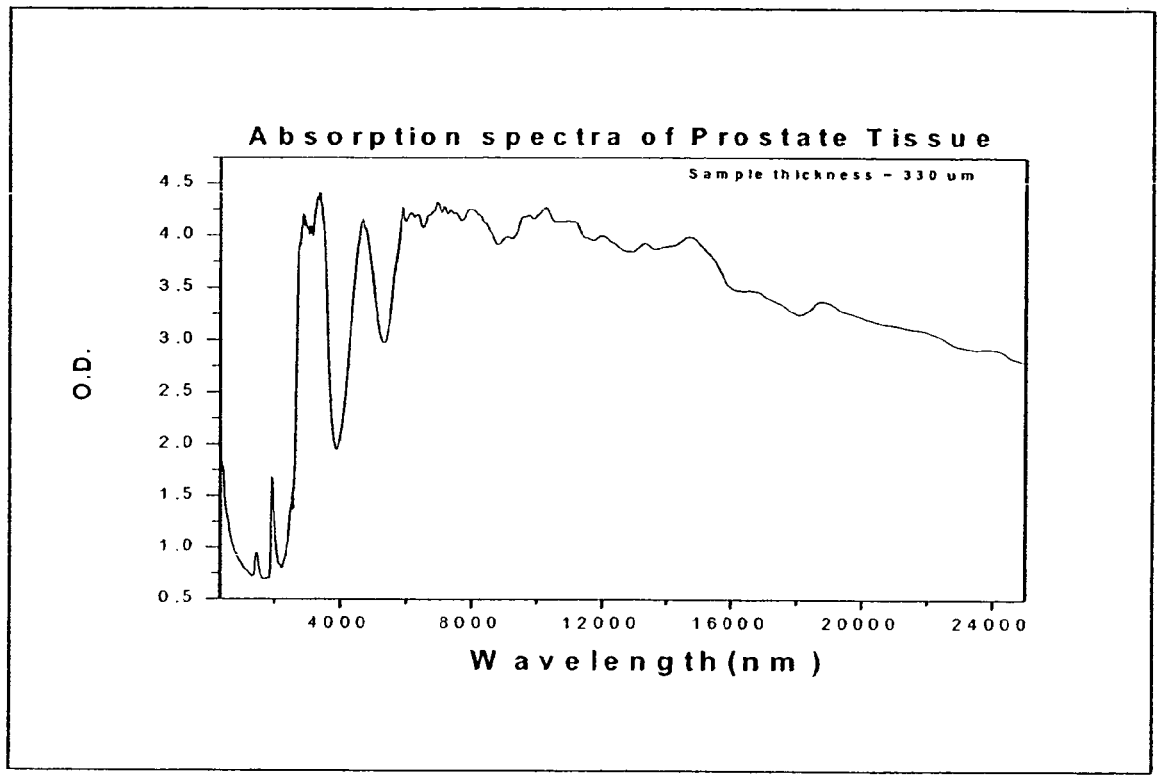
FIG. 4 is a graph showing the optical density of normal prostate tissue as a function of wavelength.
Figure 5:
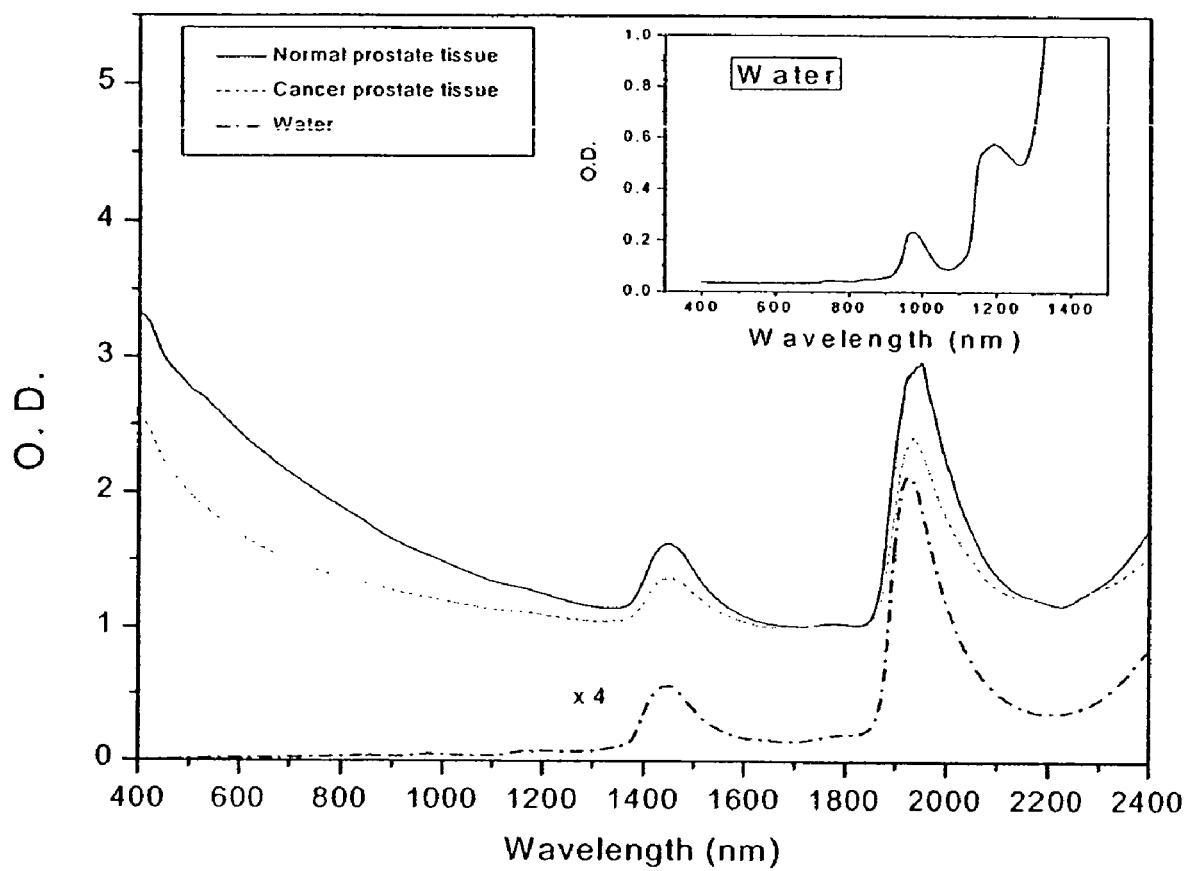
FIG. 5 is a graph comparing the optical densities of normal prostate tissue, cancerous prostate tissue (300 μm), and water as a function of wavelength, with a graphical inset showing the optical density of water (1 cm thickness) throughout a spectral range from 400 nm to 1300 nm.

FIG. 4 is a graph showing the optical density of normal prostate tissue as a function of wavelength. Wavelengths in the range of 400 to 25,000 nm were tested. FIG. 5 is a graph comparing the absorption spectra of normal prostate tissue (330 μm thickness), cancerous prostate tissue (330 μm thickness), and water (200 μm thickness) for wavelengths between 400 and 2400 nm. In the graphs of FIGS. 4 and 5, the extent of absorption at various frequencies is referred to as "optical density" (O.D.). The absorption of 1 cm thickness of water is inserted in FIG. 5. For pure water that is not associated with other molecules, the fingerprints of absorption in the spectral range of 400-2400 nm are 980 nm (very weak), 1195 nm (weak), 1444 nm (strong), and 1930 nm (very strong). Although these absorption fingerprints may shift slightly in wavelength when the water molecule is associated with tissue, these fingerprints can nonetheless be utilized as guides in detecting the water content of tissue.

The absorption of water between 400 nm-800 nm is almost flat. The absorption of water in the region of visible light is very small compared to that of longer wavelengths, such as 1444 nm and 1930 nm. The absorption at 1444 nm is due to the first overtone of —OH stretching in the water molecule. It is well known that the absorption of the stretching vibration of the O—H bond in a nonassociated (free) alcholic or phenolic hydroxyl group produces a strong band at 3600 to 3650 $cm^{-1}$ (2.78-2.74 μm, respectively) in the fundamental region and near 7100 $cm^{-1}$ (1.41 μm) in the first overtone. Reference points with low and/or no absorptions at 1700 nm, 1300 nm, 1000 nm and 800 nm are used to compare with water strong absorption bands at 1930 nm, 1440 nm, 1195 nm, and 980 nm. The graphical inset at the upper right hand corner of FIG. 5 (when FIG. 5 is oriented such that the wording appears upright) shows the optical density at spectral range from 400 nm to 1400 nm with 1 cm thickness of water. The measurements was done with 1 cm thickness of water indicating that the cancerous tissue grows in the deep prostate even a few centimeters from the surface can be determined using the water absorption peaks at 980 nm and 1195 nm. These wavelengths (such as 980 nm and 1195 nm) offer a probe of deep cancerous and precancerous tissue detection.

It is well known that scattering is a smooth function of wavelength while absorption is represented by distinct peaks substantially at one or more discrete wavelengths. The optical density spectra of cancer and normal prostate tissues shown in FIG. 5 includes sharply-peaked absorption bands superimposed on a smoothly varying background caused by the prostate tissue scattering some of the incident light. It can be concluded from the optical density graph of FIG. 5 that scattering from cancer tissue is stronger than the scattering from normal tissue in a forward direction between 400-1300 nm. Transmission (T) is related to optical density (O.D.) by the formula $T=10^{-O.D.}$, since the O.D. for normal tissues is greater than that of the cancer tissues then the transmission of normal tissues is less than that of cancer. This is due to two main factors: absorption and scattering. In the 400-1300 nm region, the signal is mainly due to scattering. The received light intensity from cancerous tissues is larger than the received light intensity from normal tissues in a forward direction since the O.D. of the cancerous tissues is smaller than that of normal tissues. Images using CCD camera 219 (FIG. 3) show more light intensity from cancerous tissues than normal tissues in the forward direction. This phenomenon arises from the fact that the sizes of cells and structures in cancerous tissue are larger than those of normal tissues. Observations confirm Mie theory: the larger the particle size, the greater is the forward scattering. Light transmission through cancerous tissues is greater than that for normal tissues, as shown in the transmission mode images of FIG. 9. The forward scattered light from cancerous tissue arrives earlier than light that travels through normal tissue, while at large angles, normal tissue scatters light more strongly than cancerous tissue.

The nuclei of both cancerous and normal cells are considered to be large particles, much larger than the visible to near infrared wavelengths employed by the imaging process. Accordingly, these nuclei obey Mie scattering, resulting in a strong forward scattering of light. The scattering angle $\theta_S$ can be written in terms of scattering wavelength ($\lambda$) and the size of the scatterer (a) as $$\theta_S \sim \frac{\lambda}{a}.$$

The sizes of structures and cells for cancer are larger; therefore, the scattering angle ($\theta_S$) is small for cancerous cells, giving a larger intensity in the forward direction. Normal cells will scatter light at larger angles than cancerous cell tissues. For objects having smaller scattering sizes, such as mitochondria (much smaller than normal size), scattering in the backward direction is larger, giving a stronger signal for scattering off small structures.

At 1456 nm and 1944 nm, absorption dominates, such that absorption is stronger than scattering. The graphs of FIGS. 4 and 5 show absorption of normal tissue is stronger than that of cancerous tissue at 1456 nm and 1944 nm, which indicates that the content of water in normal tissues is greater than that of cancer tissues. The peaks of around 1456 nm and 1944 nm in prostate tissue are due to water-tissue interaction, resulting in a wavelength shift toward longer wavelengths due to the stretching frequency of a bonded OH group (causing a shift towards the lower wave numbers). This wavelength shift is probably caused by the higher order phases of water and their interactions with cellular or other macromolecules in prostate tissues.

Figure 6:
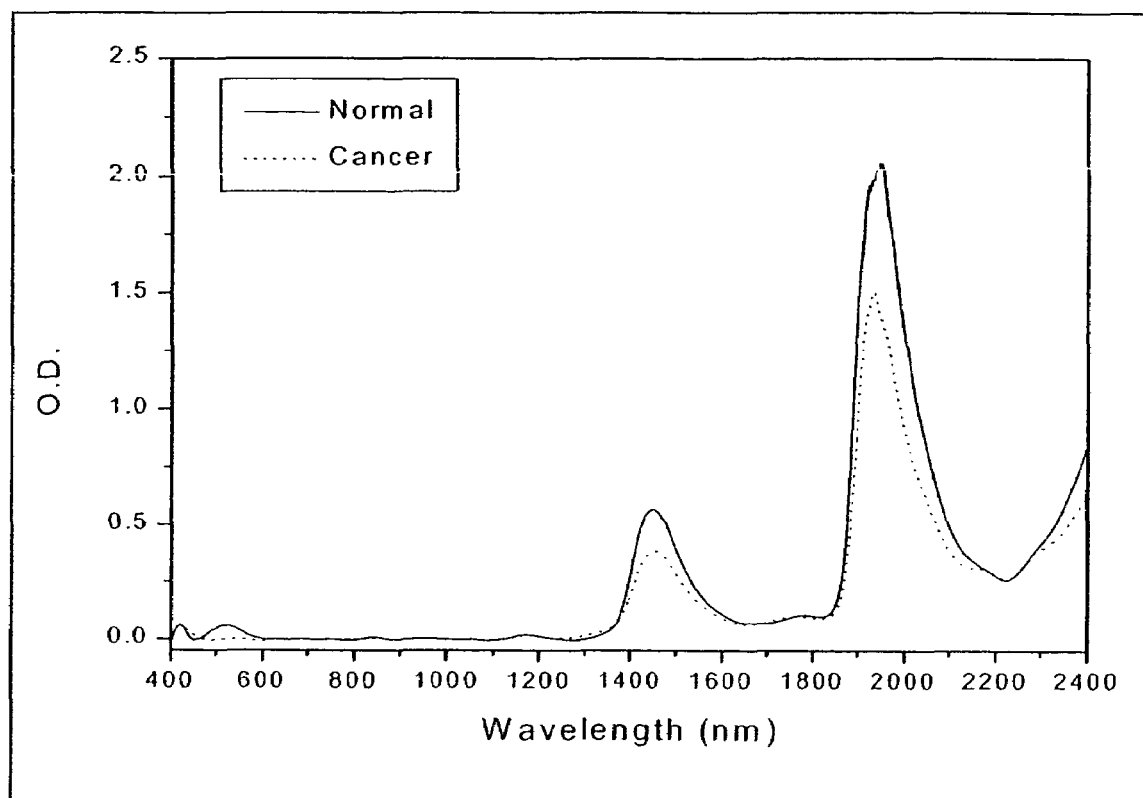
FIG. 6 is a graph comparing the optical densities of normal prostate tissue and cancerous prostate tissue as a function of wavelength.

The calculated extinction coefficients of water at different wavelengths are given in Table 1. The extinction coefficient of water at 700 nm is approximately 0.433 $cm^{-1}$ (the attenuation length about 2.31 cm), 1.29 $cm^{-1}$ at 1200 nm, and 9.7 $cm^{-1}$ at 1450 nm. The attenuating length at 1450 is approximately 7.5 times shorter than that at 1200 nm and approximately 22 times shorter than 700 nm in water. To reduce the effect of scattering in the profile shown in FIG. 5, a smooth fitted curve that reflects the contribution of scattering is subtracted from the original curve. The result is shown in FIG. 6. The absorption fingerprints in the visible region are 420 nm and 570 nm, which is due to the blood in the tissue matrix (Hb and $HbO_2$).

In cancerous tissue, the path length (equal to $1/\mu_t$) at 1450 nm is approximately 1.2 times shorter than at 1200 nm whereas, in normal tissue, the path length at 1450 nm is approximately 1.3 times shorter than at 1200 nm. The total attenuation coefficient of normal tissue is larger than that of cancerous tissue (as seen in Table 1). The path length of normal tissue is shorter than that of cancerous tissue. This signifies that photons traversing through normal tissue will be absorbed or scattered at a shorter distance than would be the case in cancerous tissue. The attenuating length $$\left(l_t = \frac{1}{n\sigma}\right)$$

is inversely proportional to the number of particles per unit volume (n) and the cross section of the scatterer (σ). Since the cross section of cancer cells (larger nucleus) is larger than that of normal cells and the attenuation length of normal tissues is smaller than that of cancerous tissues (Table 1), the number of normal cell nuclei per unit volume must be larger than that for cancerous tissues ($n_n)n_c$).

Figure 7:
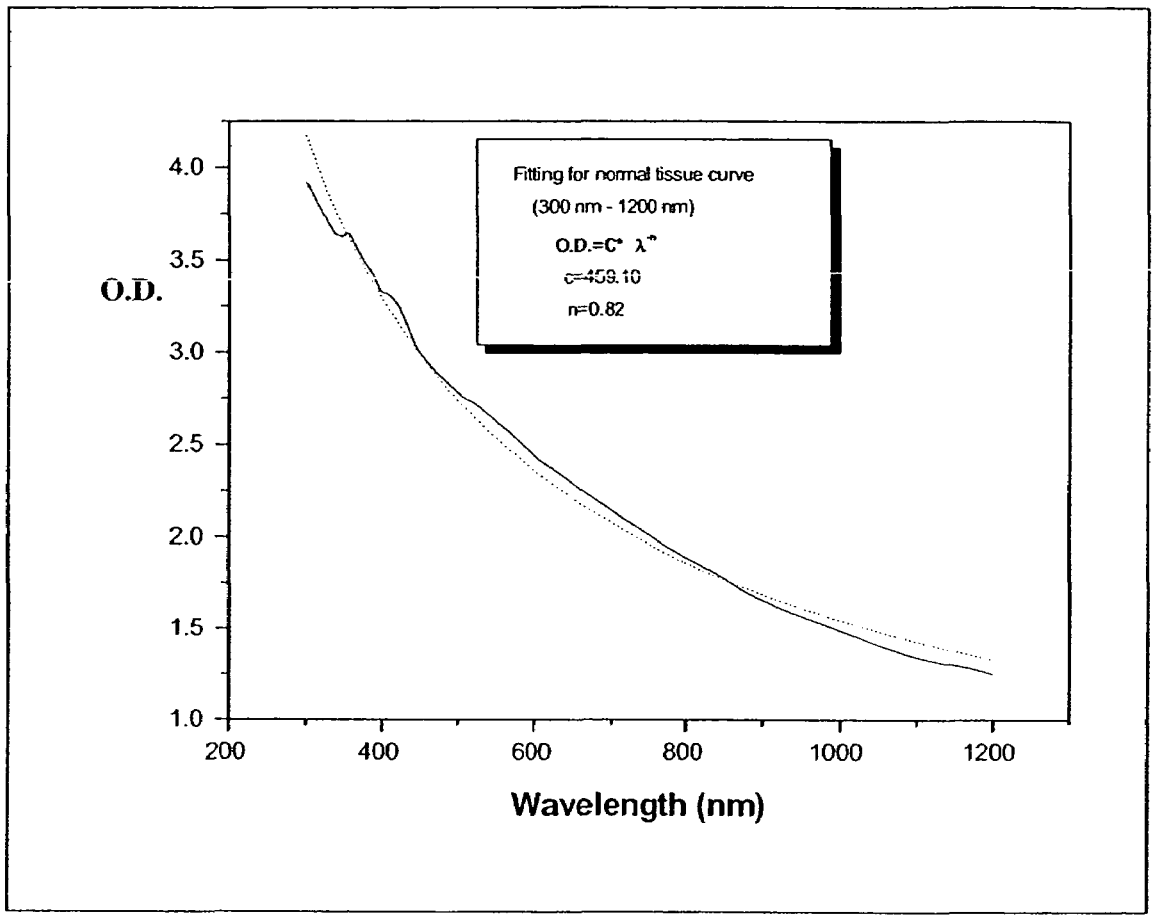
FIG. 7 is a graph showing curve fitting for optical density as a function of wavelength for normal tissue.
Figure 8:
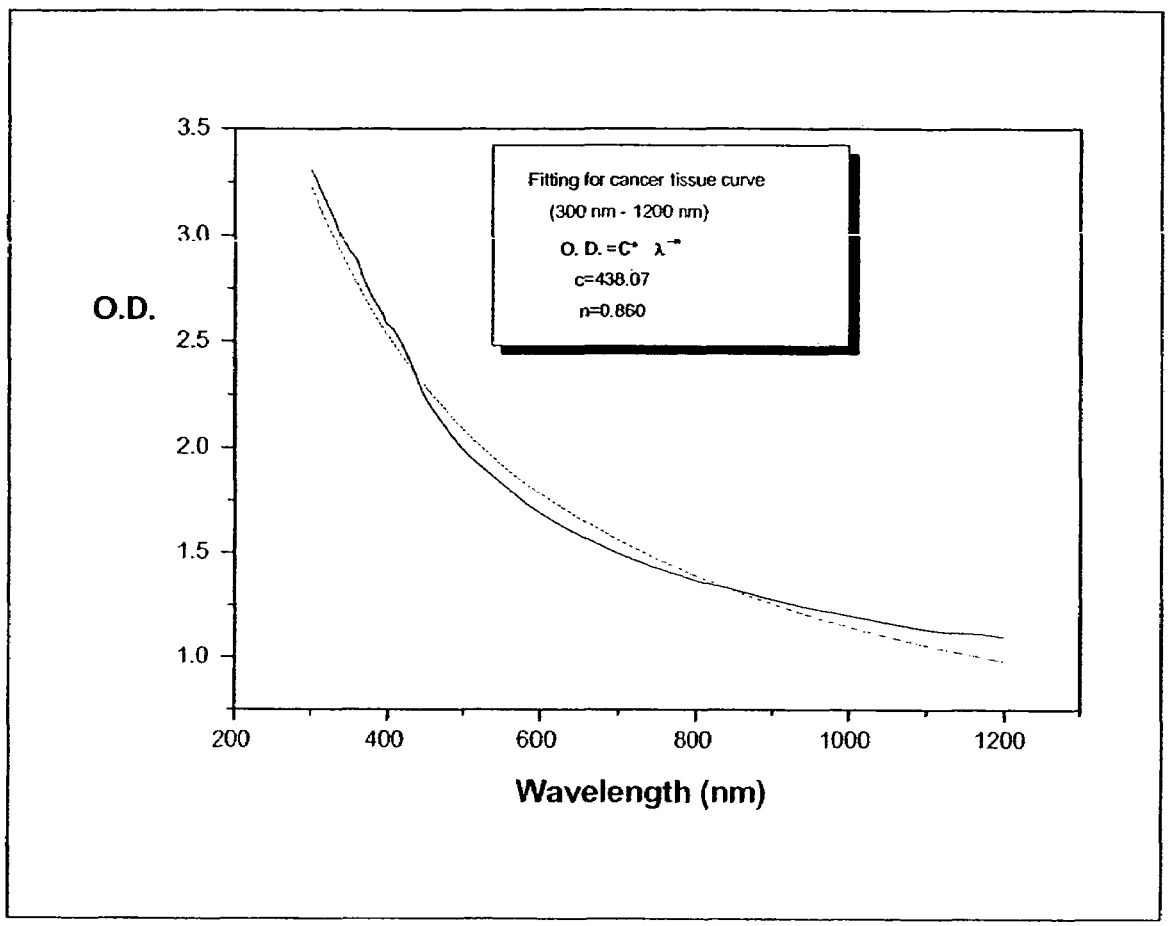
FIG. 8 is a graph showing curve fitting for optical density as a function of wavelength for the cancerous tissue.

The attenuation intensity of prostate tissues in 400-1200 nm was fitted to $C\lambda^{-n}$. In this fitting, n takes approximately the value of 0.82 for normal tissues and 0.86 for cancerous tissues, with different values for the C factor as shown in FIGS. 7 and 8, respectively. The n values for both normal and cancerous tissues are close.

The scatterer size (d) of the nucleus to the wavelength (λ) (at ~1 μm) is approximately 5 times (d/λ~5) in the normal cell and 10 times (d/λ~10) in the cancerous cell. This is the large particle case (Mie theory), where the scattering is stronger in the forward direction in both cases. When n=4 (in $C\lambda^{-n}$), as in the case of very small particles (compared to the incident wavelength), this represents a scenario where Raleigh scattering dominates. It is expected that, for larger particles, n becomes a smaller value, so as to reduce the scattering coefficient, as this is related to scattering intensity.

FIG. 9 shows eight transmission images, labelled a-h, of cancerous and normal tissue samples at 700 nm, 800 nm, 1200 nm, and 1450 nm for parallel and perpendicular orientations of tissue. The left piece of the specimen (predominately normal tissue) has less transmission intensity than that on the right side (predominately cancer) at all wavelengths (700 nm, 800 nm, 1200 nm, and 1450 nm) as shown in FIG. 9. Similar results were obtained in normal and cancerous human breast tissues using picosecond temporal time gated imaging at 800 nm through the use of a Ti:sapphire pulsed laser. In the large particle case (Mie scattering), the intensity of forward scattering is higher than that of backscattering. Since the nuclei of the cancer tissues are larger than that of normal tissues, forward scattering for cancerous tissue is expected to be larger than that of normal tissue in the forward direction. At 1200 nm, scattering is stronger than absorption. The forward scattering intensity from cancer tissues at 1200 nm is higher than that of normal tissues, as shown in FIG. 5. As a result, transmission through cancerous tissues is greater than that of normal tissues, as shown in images c (parallel orientation) and g (perpendicular orientation) of FIG. 9. At 1450 nm, absorption dominates (stronger than scattering), and the absorption of normal tissue is stronger than that of cancerous tissue, as shown in FIGS. 5 and 6. The transmission intensity through normal tissues is weaker than that of cancerous tissues. At the absorption peaks of water, tissue that contains more water will absorb more incoming photons than tissue, which contains less water. Local deviations in water concentration within tissue will cause a differentiation in the degree of scattering. The changes displayed in images d and h of FIG. 9 result mainly from absorption of water in tissue (first overtone of OH stretching vibration); in addition, the forward scattering in cancerous tissues is greater than that of normal tissues.

From the curves displayed in FIGS. 5 and 6, the absorption peak at 1450 nm is stronger than that at 1200 nm. Scattering at 1450 nm is less than that at 1200 nm. Most of the photons at 1450 nm are absorbed strongly by water molecules in the prostate tissues. Photons at 1200 nm get absorbed less. Since cell nuclei are larger than the wavelength, these nuclei predominantly scatter light is in the forward direction. The scattered intensity is related to the population density of the nuclei. For the perpendicular case, depolarization is due mainly to multiple scattering events. Such depolarization, attributable to cell size, cell shape and cell water content, causes photons to be more depolarized in cancer tissue since cancer is more randomized in shape and size and includes less water content. The internal structures of the cancerous tissues randomize the light more than in the case of normal tissue. Normal tissue is highly ordered in water, as is readily observed by considering the images shown in FIG. 9.

Figure 10:
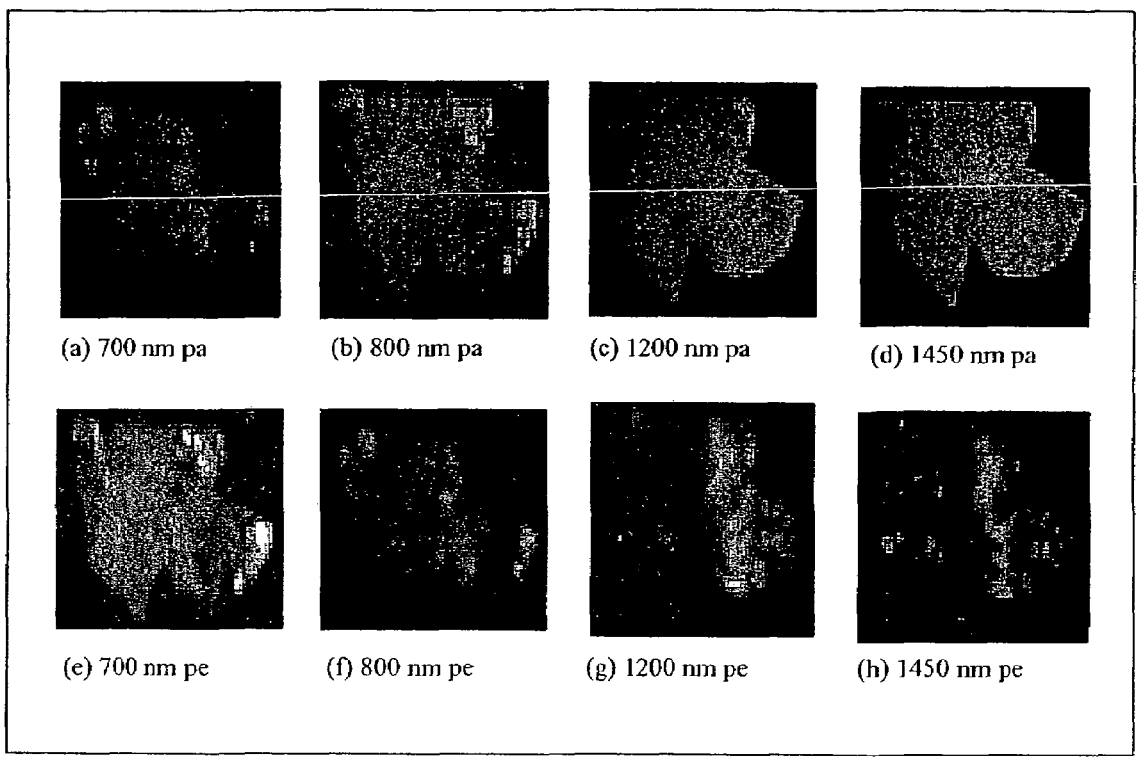
FIG. 10 shows backscattering images of the specimen of FIG. 2 at several wavelengths along a parallel plane and a perpendicular plane.

In images taken using the backscattering geometry of FIG. 3, light scattering from cancerous tissue is stronger than that of normal tissue. It is known that the index of refraction for cancerous tissue is higher than that of normal tissue for early stages of cancer (refer to equation (7) provided above). Accordingly, cancer tissue contains less water than normal tissue and, consequently, cancer tissue has higher index of refraction than normal tissue. As shown in FIG. 10, one would expect that backscattering intensity for cancerous tissue is larger than that of normal tissue, due to the fact that cancerous tissue is denser (higher index of refraction) than normal tissues, and due to the lower light attenuation at water absorption wavelengths in cancerous tissue. Moreover, smaller cellular structures, such as mitochondria, play a major role in the backscattering geometry. As a result of the foregoing factors, cancerous regions will appear brighter than normal regions.

Figure 11:
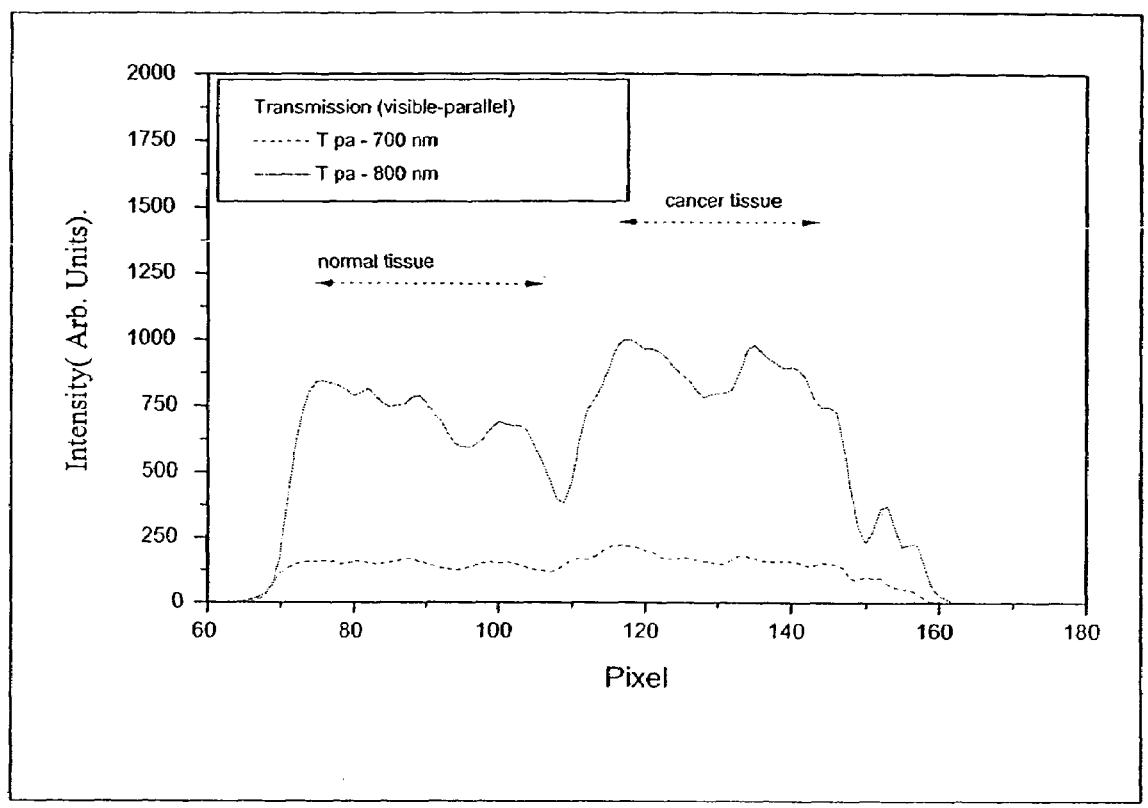
FIG. 11 is a graph showing optical intensity distribution at 700 nm and 800 nm as a function of pixels for a digitized horizontal scan from left to right at the center of the transmission images of FIG. 9.
Figure 12:
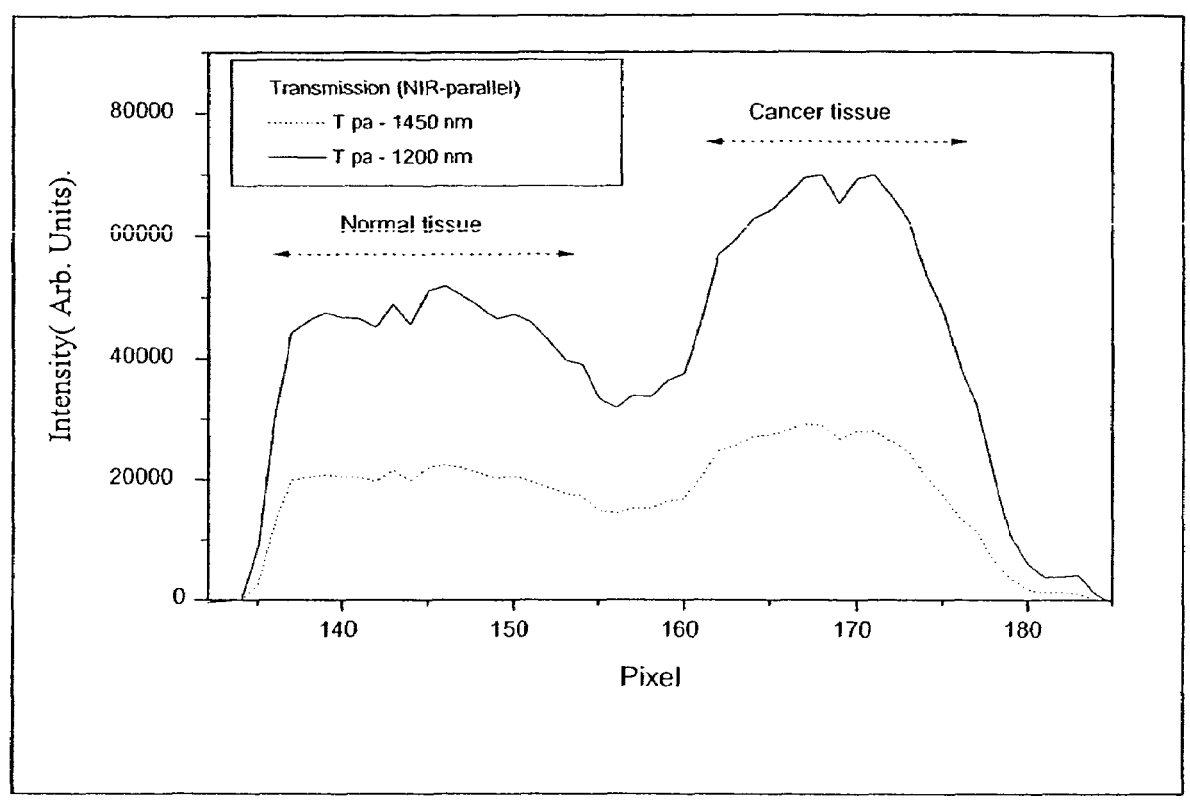
FIG. 12 is a graph showing optical intensity distribution at 1200 nm and 1450 nm as a function of pixels for a digitized horizontal scan from left to right at the center of the transmission images of FIG. 9.

A digitized horizontal scan from left to right at the center of transmission images a, b, c, and d displayed in FIG. 9 are shown in FIG. 11 (700 nm and 800 nm) and FIG. 12 (1200 nm and 1450 nm). The curves in FIGS. 11 and 12 represent the intensity distribution of images a and b, and c and d of FIG. 9, respectively. FIG. 11 shows that the region of cancerous tissue scatters more than the region of normal tissue around 700 nm and 800 nm in the forward scattering direction. The main difference between cancerous and normal tissues in the 700 nm and 800 nm regions is attributed to scattering, since absorption is almost identical in both cases. The images of FIG. 9 show that the cancerous region absorbs less light than the normal region at 1450 nm and 1200 nm, due to the water content of the tissue. Wavelengths that are not substantially absorbed by water, such as 1700 nm, 1300 nm, 1000 nm, and 800 nm can be used to generate reference images, so as to provide a basis of comparison to images generated using water absorption wavelengths. Different images at different wavelengths will provide highlights of cancer regions for diagnoses. In addition, the forward scattering of cancerous tissues is larger than that of normal tissues due to the larger size of the cellular nuclei in cancerous tissue. Accordingly, transmission through cancerous tissues is higher than that of normal tissue, as is shown in FIG. 9. At a wavelength of 1450 nm, absorption dominates, so the primary reason for higher transmission in cancerous regions is due to less water content in cancerous tissue relative to regions of normal tissue, which in turn, is related to the microscopic bonding of OH in cancerous tissue.

A linearly polarized light incident on tissue loses its polarization as it traverses the medium. A portion of the incident light is backscattered by the tissue surface, retaining its polarization in this single scattering event. The remaining light propagating in a turbid medium, such as prostate tissue, can be viewed as consisting of three components: ballistic, snake and diffusive. Diffusive light is the dominant component, consisting of multiple-scattered photons that travel the longest path and, consequently, take the longest time to exit the sample. Ballistic photons traverse the shortest path, retain most characteristics of the incident photons, and carry direct information about the interior structure of the scattering medium. Snake photons follow ballistic photons in time and are involved in fewer scattering events; they retain a significant amount of the initial properties and information on structures hidden in the scattering medium.

The calculated degree of polarization (D as written in equation 5) for normal and cancerous tissues at different wavelengths using the data shown in FIGS. 11 and 12 is shown in Table 2. The values of D for normal tissues are higher than that of tissues at all wavelengths (700 nm, 800 nm, 1200 nm, and 1450 nm). This result is due to greater randomization (abnormal growth) of cancerous cells, whereas normal cells are more ordered. The degree of polarization of cancerous and normal tissues increases as the wavelength increases. The degree of polarization ratio for 1450 nm to 1200 nm is approximately 1.1 for normal tissues and 1.7 for cancerous tissues, which suggests that the water content of prostate tissue affects the degree of polarization. The OH vibrational mode at 1450 nm plays an important role in both cancerous and normal tissues. The degree of polarization for both normal and cancerous tissues at 1450 nm is due to strong absorption bonding. While at 1200 nm the OH vibrational mode is weak and macroscopic scattering dominates, so the shape and size play a very important role. In both cases, the degree of polarization of cancer is less than that of normal ($D_{cancer} < D_{normal}$).

The calculated contrasts (C as written in equation 6) between cancer and normal tissues are 0.11 at 700 nm and 800 nm, 0.17 at 1200 nm, and 0.15 at 1450 nm. The main difference between 1200 nm and 1450 nm contrasts is that at 1450 nm, the resulting contrast is due to microscopic OH bonding in prostate tissue, while at 1200 nm the difference is due to macroscopic scattering size and population density in the prostate tissue.

The absorption spectrum and imaging measurements clearly show that the water fingerprint absorption peaks at 980 nm, 1195 nm, 1456 nm, 1944 nm, 2880-3600 nm, and 4720 nm can be used to determine the water contents of tissues and diagnose the cancerous tissue. Among these wavelengths, absorption peaks at 980 nm and 1195 nm can be used to detect deep cancerous and precancerous growing tissues a few centimeters deep from the surface of the prostate (as shown in the graphical inset of FIG. 5). Other wavelengths of 1456 nm, 1944 nm, 2880-3600 nm and 4720 nm can be used to detect cancerous tissues growing on the surface and subsurface of the prostate, or in thin sections of tissue used in pathology.

Similar to the digital rectal examination through rectum for checking an abnormal prostate in clinical, the best way to optically image prostate tumors is illuminating and imaging the prostate gland through rectum. For this reason, we have imaged objects hidden inside prostate tissues through rectum-membrane-prostate tissues.

Figure 13:
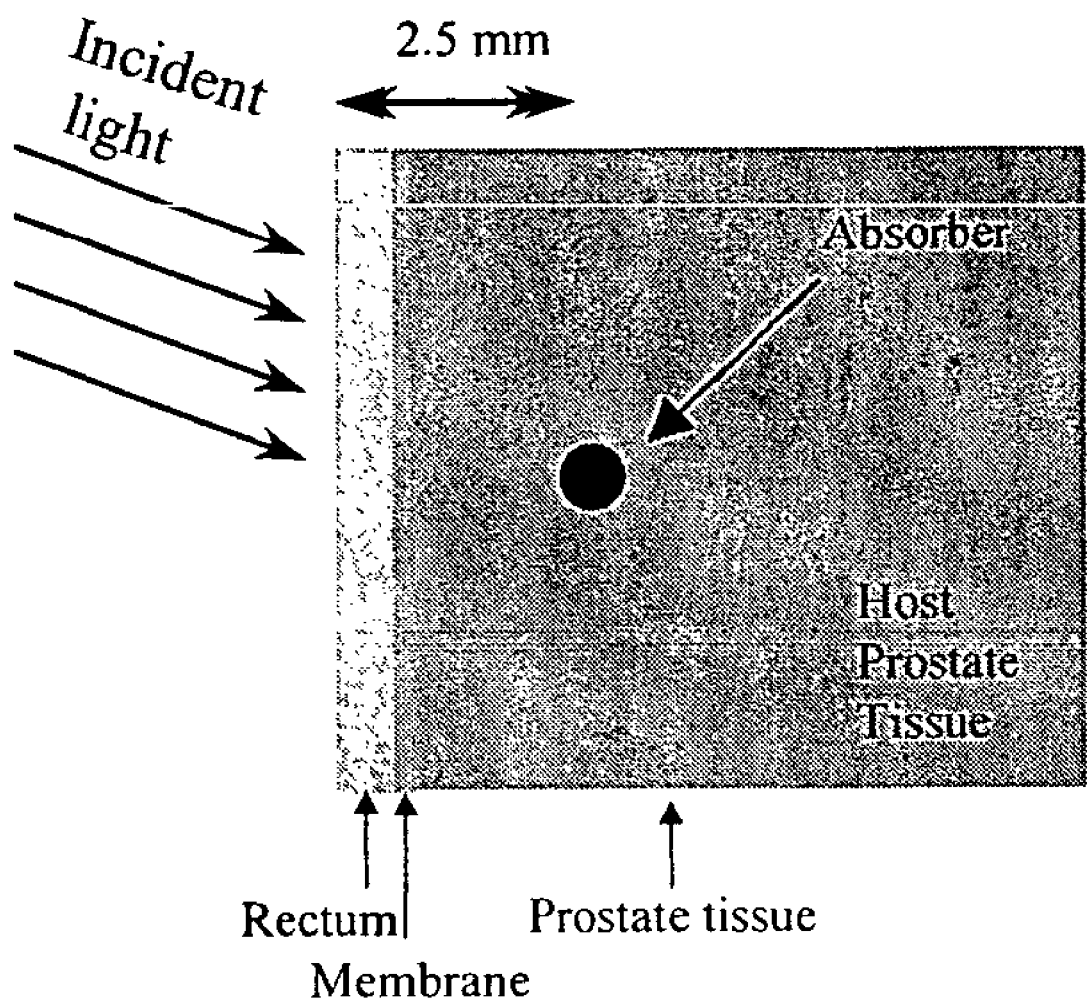
FIG. 13 is a layer structure of a model rectum-membrane-prostate tissue sample made of a small dot piece of black absorber embedded inside a larger piece of host prostate tissue in a rectum-membrane-prostate tissue structure at a depth of 2.5 mm from the surface of the rectum.

The sample used for the scattered light imaging measurements consisted of a small piece of absorber (~1 mm) embedded inside a large slice of prostate tissue (~30×20 mm) in a rectum-membrane-prostate structure with a depth of ~2.5 mm from the surface of the rectum-membrane-prostate tissue structure [see FIG. 13]. During the measurements, the illumination and detection wavelengths (as an example at 600 nm, 700 nm, and 800 nm) were synchronously changed so that the detection wavelengths were always kept the same as that of illumination.

Figure 14:
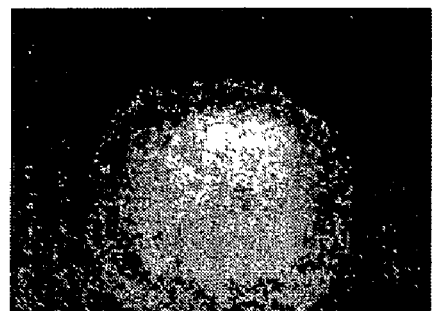
FIGS. 14(a) thru 14(c) show scattered light images recorded at wavelengths of (a) 600 nm, (b) 700 nm, and (c) 800 nm, respectively, where P and D are is the pump and detection wavelengths, respectively.
Figure 14:
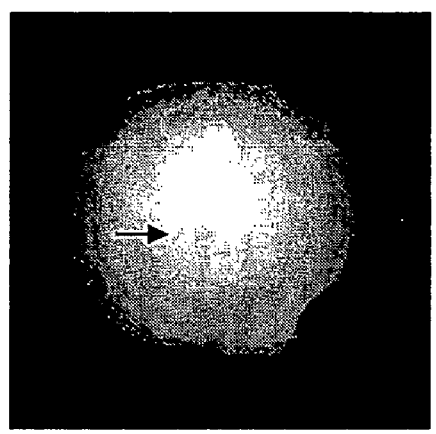
Figure 14:
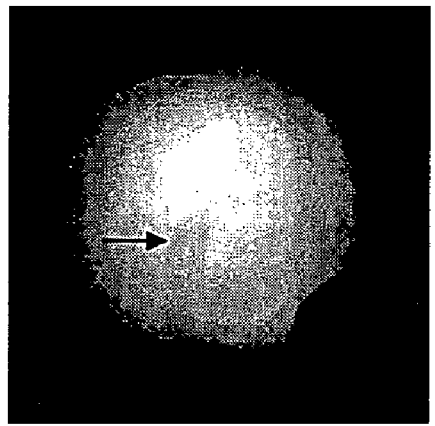

The scattered light images recorded at the wavelengths of 600 nm, 700 nm, and 800 nm with the detection polarization perpendicular to that of illumination are shown in FIGS. 14(*a*)-14(*c*). It can be seen that the object (absorber) cannot be distinguished by the 600 nm image, but it can be clearly identified as a dark point by the 800 nm image. As the wavelength increases from 600 nm to 800 nm, the visibility of the object improves. The wavelength dependence of the image quality of the scattered light images can be explained by the relative absorption spectra of the prostate and rectum tissues, which was shown in FIG. 5. The relative absorptions of the prostate and rectum tissues decrease when the wavelength increases from 400 nm to NIR. The short wavelength (such as 600 nm) light was absorbed and scattered strongly by the surface and near surface layers of the rectum-membrane-prostate tissues, and could not reach the object deeply embedded in the host prostate tissue. In this case, the scattered light images are formed by the light scattered only from the surface and near surface tissue layers with almost no contribution from the object, and therefore, the object cannot be identified. In contrast, the larger penetration of the longer wavelength NIR light in rectum-membrane-prostate tissues enables them to reach the deeper object. Once the NIR light reaches the object, the difference of scattering and absorption properties between the foreign object and the surrounding tissues is reflected in the image, and therefore, the foreign object can be identified by the NIR scattering images.

Our results indicate the possibility of the spectral polarization optical imaging technique for detecting small objects and structural changes in prostate tissues through rectum-membrane-prostate tissues, and the potential of imaging and detecting prostate cancers through rectum in real time without removing tissues using the key water absorption wavelengths.

It is clear that images at other wavelengths such as 1195 nm, 1456 nm, 1944 nm, 2880 nm, and 4720 nm are suitable to distinguish cancer from normal prostate tissues due to the difference of cancerous and normal prostate tissues in water concentrations as explained earlier.

Figure 15:
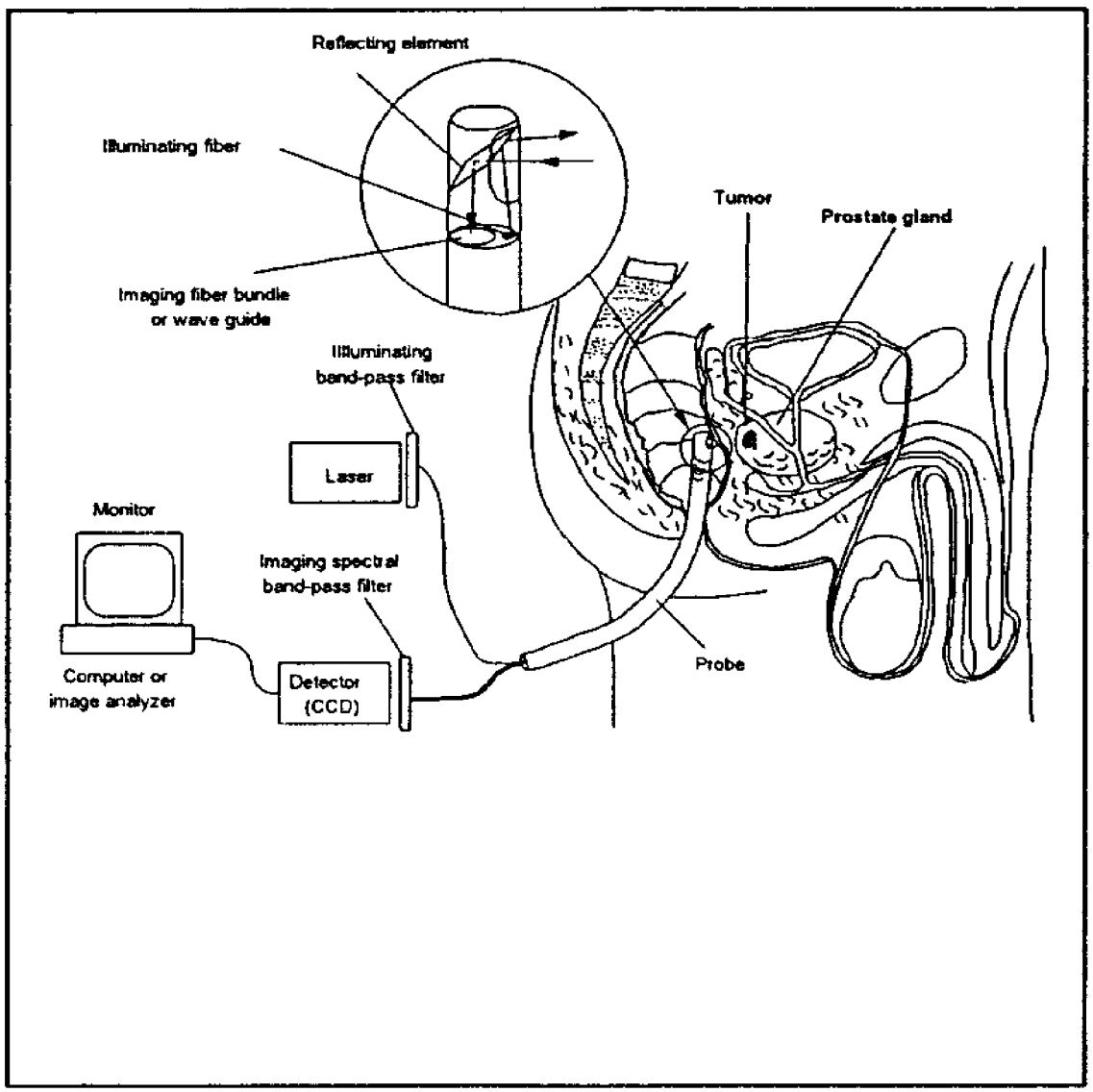
FIG. 15 shows a schematic diagram of an optical fiber-probed NIR polarization imaging instrument for prostate cancer detection through rectum.

Detecting of prostate tumors using the optical rectal coherent fiber-probed spectral polarization imaging instrument is shown in FIG. 15. The illuminating light reaches the rectum and prostate through an optical coherent fiber-bundle probe. The Light back-scattered from the prostate is collected by a coherent fiber-bundle. An image-collecting coherent fiber-bundle is coupled into a CCD detector after the collected light passes through band pass filters. A polarizer (linear and/or circular polarization element) for the incident beam is coupled into a fiber. The backscattered light from the prostate is collected by a probe using a polarization preserving fiber. The image-collection coherent fiber-bundle is coupled into NIR and Mid-IR CCD camera after the collected light passes through a detecting polarizer (linear and/or circular polarization element) called analyzer. The analyzer can be rotated in the parallel or perpendicular polarization direction relative to the incident polarized beam. Since the NIR and Mid-IR polarization images have high spatial resolution and contrast, a small prostate cancer, which cannot be detected by other methods, may be visualized from these optical images.

We claim:

1. A minimally invasive method for enabling detection of cancerous tissues, the method comprising the steps of
   (a) performing spectral optical imaging of a tissue substantially at one or more peak water absorption wavelengths to generate a water absorption image;
   (b) performing spectral optical imaging of the tissue at one or more wavelengths of low or negligible water absorption to generate a reference water absorption image; and
   comparing the generated water absorption and reference water absorption images so as to identify any substantial difference in water content between a first region of the tissue and a second region of the tissue, such that changes in water content in normal and cancerous tissues at a same water absorption peak wavelength become detected, wherein steps (a) and (b) are performed simultaneously or successively in any order.

2. The method of claim 1 wherein the one or more wavelengths of lower or negligible water absorption include at least one of 4500 nm, 2230 nm, 1700 nm, and 1300 nm.

3. The method of claim 1 further including the step of generating a difference image from the water absorption image and the reference water absorption image.

4. The method of claim 1 wherein steps (a) and (b) are used to diagnose one or more regions of cancerous tissue in a human prostate by using at least one of: (i) one or more water absorption peaks at 1195 nm for deep prostate cancer detection, and (ii) one or more water absorption peaks at, 1944 nm, 2880-3600 nm, and 4720 nm for surface and subsurface prostate cancer detection or pathology of thin slices of tissues.

5. The method of claim 1 wherein steps (a) and (b) are used to diagnose one or more regions of cancerous tissue in at least one of skin, a cervix, a human breast, and other human organs.

6. A minimally invasive method for enabling detection of tissue in cancerous or precancerous tissues, the method comprising the steps of:
   (a) performing spectral optical imaging of a tissue substantially at one or more peak water absorption wavelengths including at least one of 1195 nm, 1944 nm, 2880 nm to 3360 nm, and 4720 nm, to generate a water absorption image so as to enable an identification of any regions of the tissue in terms of the water content;
   (b) performing spectral optical imaging of the tissue at one or more wavelengths of low or negligible water absorption including at least one of 4500 nm, 2230 nm, 1700 nm, and 1300 nm, to generate a reference water absorption image;
   wherein steps (a) and (b) are performed simultaneously or successively in any order to enable a comparison of the generated water absorption and reference water absorption images so as to identify any substantial difference in water content between a first region of the tissue and a second region of the tissue.

7. The method of claim 6 further including the step of generating a difference image from the water absorption image and the reference water absorption image.

8. The method of claim 6 wherein steps (a) and (b) are used to diagnose one or more regions of cancerous tissue in a human prostate by using at least one of (i) one or more water absorption peaks at and 1195 nm for deep prostate cancer detection, and (ii) one or more water absorption peaks at, 1944 nm, 2880-3600 nm, and 4720 nm for surface and subsurface prostate cancer detection or pathology of thin slices of tissues.

9. The method of claim 6 wherein steps (a) and (b) are used to diagnose one or more regions of cancerous tissue in at least one of skin, a cervix, a human breast, and other human organs.

10. A spectral optical imaging system comprising:
    a source of infrared illumination;
    first and second polarizers;
    first and second wideband filters; and
    a charge-coupled device (CCD) camera,
    wherein the source is equipped to illuminate a tissue to be diagnosed through the first wideband filter and the first polarizer, the CCD camera is equipped to receive at least one of transmitted light and back-scattered light from the tissue through the second wideband filter and second polarizer, the first and second wideband filters include a selection mechanism enabling selection of at least one water absorption wavelength and at least one reference water absorption wavelength, the water absorption wavelength including at least one of 1195 nm, 1944 nm, 2880-3600 nm, and 4720 nm, to generate a water absorption image, and the reference water absorption wavelength including at least one infrared wavelength that provides negligible water absorption, the at least one infrared wavelength that provides negligible water absorption including at least one of 4500 nm, 2230 nm, 1700 nm, 1300 nm, 1000 nm, and 800 nm, to generate a reference water absorption image; and
    a processing mechanism configured to compare the generated water absorption and reference water absorption images.

11. The spectral optical imaging system of claim 10, wherein said system performs minimally invasive detection of cancerous tissues by:
    (a) the CCD camera performing spectral optical imaging of a tissue substantially at one or more peak water absorption wavelengths by adjusting the first and second wideband filters to pass electromagnetic energy at least one of, 1195 nm, 1944 nm, 2880 nm to 3360 rim, and 4720 nm, to generate a water absorption image so as to enable an identification of any regions of the tissue which have different water content relative to other regions;
    (b) the CCD camera performing spectral optical imaging of the tissue at one or more wavelengths of low or negligible water absorption by adjusting the first and second wideband filters to pass electromagnetic energy at the one or more low or negligible water absorption wavelengths, the one or more wavelengths of, negligible water absorption include at least one of 4500 nm, 2230 nm, 1700 nm, 1300 nm, 1000 nm, and 800 to generate a reference water absorption image so as to enable an identification of any regions of the tissue which have a different water content relative to other regions;
    wherein the CCD camera generates the reference image and the water absorption image simultaneously or successively in any order, thereby enabling a comparison of the reference water absorption image and the water absorption image to identify any substantial difference in water content between a first region of the tissue and a second region of the tissue.

12. The spectral optical imaging system of claim 11 wherein the one or more wavelengths of low or negligible water absorption include at least one of 4500 nm, 2230 nm, 1700 nm, and 1300 nm.

13. The spectral optical imaging system of claim 11 wherein the processing mechanism includes a graphical processing mechanism for generating a difference image from the water absorption image and the reference water absorption image on a pixel-by-pixel basis.

14. The spectral optical imaging system of claim 11 wherein the reference water absorption image and the water absorption image are used to diagnose one or more regions of cancerous tissue in a human prostate by using at least one of: (i) one or more water absorption peaks at 1195 nm for deep prostate cancer detection, and (ii) one or more water absorption peaks at 1944 nm, 2880-3600 nm, and 4720 nm for surface and subsurface prostate cancer detection; and comparing one or more images generated using one or more water absorption peaks with one or more images generated at wavelengths having no or negligible water absorption.

15. The spectral optical imaging system of claim 11 wherein the processing mechanism is configured to use the reference water absorption image and the water absorption image are used to diagnose one or more regions of cancerous tissue in at least one of skin, a human breast, a cervix, and other human organs.

16. The spectral optical imaging system of claim 11 wherein the source is an LED (light emitting diode) or white light source, the system further comprising a coupling mechanism for coupling the source to a tissue through an optical subsystem including at least one of a filter, a lens, a mirror, a beam splitter, a polarizer, optical fiber, a CCD detector, and a CMOS detector.

17. The spectral optical imaging system of claim 11 wherein the CCD camera is a sensitive red visible to mid-IR CCD or CMOS camera system.

18. The spectral optical imaging system of claim 11 further comprising a computerized imaging system coupled to the CCD camera, the computerized imaging system including a processing mechanism for executing data collection software and for posting images to a display screen.

19. The spectral optical imaging system of claim 11 wherein an optical fiber probe is inserted rectally to provide rectal illumination and collect the reference water absorption and water absorption images to detect prostate cancer.

20. The spectral optical imaging system of claim 11, wherein the reference water absorption image and the water absorption image permit a diagnosis of one or more regions of cancerous tissue in a human prostate by using at least one of: (i) one or more water absorption peaks at 1195 nm for deep prostate cancer detection, and (ii) one or more water absorption peaks at 1944 nm, 2880-3600 nm, and 4720 nm for surface and subsurface prostate cancer detection; and comparing one or more images generated using one or more water absorption peaks with one or more images generated at wavelengths having no or negligible water absorption.

21. The spectral optical imaging system of claim 10 wherein the processing mechanism includes a graphical processing mechanism for subtracting the water absorption images from the reference water absorption images so as to enable a correlation of a tissue to be diagnosed with any one of three states including normal, benign, and cancerous tissues, wherein the graphical processing mechanism is programmed to perform the subtracting such that:

$$\pm I(\lambda_{NW}) \mp I(\lambda_W) = \Delta I \quad \text{represents a plurality of spectra or images}$$

$$\text{and } \frac{I(\lambda_{NW})}{I(\lambda_W)} = RI \quad \text{represents a ratio spectra of images}$$

where $\lambda_W$ represents one or more water absorption wavelengths, $\lambda_{NW}$ represents one or more reference wavelengths having no or negligible water absorption, and $\Delta$ is an intensity difference between the water absorption image and the reference water absorption image.

22. The spectral optical imaging system of claim 10 further including a configuration adjustment mechanism for providing each of the water absorption image and the reference water absorption image in a parallel geometry and a perpendicular geometry, wherein the parallel and perpendicular geometries are determined with reference to orientation of the CCD camera, so as to permit a determination of polarization dependency for the water absorption image and the reference water absorption image.

23. The spectral optical imaging system of claim 10, wherein the system performs a minimally invasive detection of cancerous tissues by:
(a) the CCD camera performing spectral optical imaging of a tissue substantially at one or more key water absorption wavelengths by adjusting the first and second wideband filters to pass electromagnetic energy at least one of 1195 nm, 1944 nm, 2880 nm to 3360 nm, and 4720 nm, to generate a water absorption image so as to enable an identification of any regions of the tissue which have at least one of: (i) a lower water content and (ii) a higher water content, relative to other regions;
(b) the CCD camera performing spectral optical imaging of the tissue at one or more wavelengths of low or negligible water absorption by adjusting the first and second wideband filters to pass electromagnetic energy at one or more low or negligible water absorption wavelengths, the one or more wavelengths of negligible water absorption including at least one of 4500 nm, 2230 nm, 1700 nm, 1300 nm, 1000 nm, and 800 nm, to generate a reference water absorption image so as to enable an identification of any regions of the tissue which have at least one of: (i) a lower water content and (ii) a higher water content, relative to other regions;
wherein the CCD camera generates the reference water absorption image and the water absorption image simultaneously or successively in any order to perform a comparison of the reference water absorption image and the water absorption image so as to identify any substantial difference in water content between a first region of the tissue and a second region of the tissue.

24. A minimally invasive method for enabling detection of cancerous tissues, the method comprising the steps of:
(a) performing spectral optical imaging of a tissue substantially at one or more peak water absorption wavelengths to generate a water absorption image so as to enable an identification of any regions of the tissue which have at least one of: (i) less water content, and (ii) more water content, relative to other regions;
(b) performing spectral optical imaging of the tissue at one or more wavelengths of low or negligible water absorption to generate a reference water absorption image so as to enable an identification of any regions of the tissue which have at least one of: (i) a lower water content, and (ii) a higher water content, relative to other regions;
wherein steps (a) and (b) are performed simultaneously or successively in any order to compare the generated water absorption image and reference water absorption images so as to identify any substantial difference in water content between a first region of the tissue and a second region of the tissue at a same water absorption peak wavelength, such that, if a first region of tissue has a substantially lower water content than a second region of tissue, the first region of tissue is diagnosed as a cancerous or precancerous tissue region in an early stage of cancer and if the first region of tissue has a substantially higher water content than a second region of tissue, then the first region of tissue is diagnosed as a cancerous or precancerous region in a later stage of cancer.

25. The method of claim 24, wherein the tissue is breast tissue.

26. A minimally invasive method for enabling detection of cancerous prostate tissues, the method comprising the steps of:
(a) performing spectral optical imaging of a tissue substantially at one or more key water absorption wavelengths including at least one of 1195 nm, 1944 nm, 2880 nm to 3360 nm, and 4720 nm, to generate a water absorption image so as to enable an identification of any regions of the tissue which have at least one of: (i) less water content, and (ii) more water content, relative to other regions;
(b) performing spectral optical imaging of the tissue at one or more wavelengths of low or negligible water absorption including at least one of 4500 nm, 2230 nm, 1700 nm, 1300 nm, 1000 nm, and 800 nm, to generate a reference water absorption image so as to enable an identification of any regions of the tissue which have at least one of: (i) lower water content, and (ii) higher water content, relative to other regions;
wherein steps (a) and (b) are performed simultaneously or successively in any order to compare the generated water absorption and reference water absorption images so as to identify any substantial difference in water content between a first region of the tissue and a second region of the tissue at a same water absorption peak wavelength, such that, if a first region of tissue has a substantially lower water content than a second region of tissue, the first region of tissue is diagnosed as a cancerous or precancerous prostate tissue region in an early stage of cancer and if the first region of tissue has a substantially higher water content than a second region of tissue, then the first region of tissue is diagnosed as a cancerous or precancerous prostate region in a later stage of cancer.

* * * * *